(12) United States Patent
Malhotra et al.

(10) Patent No.: US 11,224,591 B2
(45) Date of Patent: Jan. 18, 2022

(54) PHARMACEUTICAL COMPOSITIONS COMPRISING RIFAXIMIN

(71) Applicant: Cipla Limited, Maharashtra (IN)

(72) Inventors: Geena Malhotra, Maharashtra (IN); Kalpana Joshi, Maharashtra (IN); Jeevan Ghosalkar, Maharashtra (IN)

(73) Assignee: Cipla Limited, Maharashtra (IN)

( * ) Notice: Subject to any disclaimer, the term of this patent is extended or adjusted under 35 U.S.C. 154(b) by 0 days.

(21) Appl. No.: 16/341,333

(22) PCT Filed: Oct. 13, 2017

(86) PCT No.: PCT/IN2017/050468
§ 371 (c)(1),
(2) Date: Apr. 11, 2019

(87) PCT Pub. No.: WO2018/069938
PCT Pub. Date: Apr. 19, 2018

(65) Prior Publication Data
US 2020/0046688 A1 Feb. 13, 2020

(30) Foreign Application Priority Data
Oct. 14, 2016 (IN) .............................. 201621035173

(51) Int. Cl.
*A61K 31/437* (2006.01)
*A61K 31/4525* (2006.01)
*A61K 9/08* (2006.01)
*A61K 9/20* (2006.01)
*A61K 9/48* (2006.01)

(52) U.S. Cl.
CPC ........ *A61K 31/437* (2013.01); *A61K 31/4525* (2013.01); *A61K 9/08* (2013.01); *A61K 9/20* (2013.01); *A61K 9/48* (2013.01)

(58) Field of Classification Search
CPC .. A61K 31/437; A61K 31/4525; A61K 47/22; A61K 9/0095; A61K 9/20; A61K 9/2013; A61K 9/48; A61K 9/4858
See application file for complete search history.

(56) References Cited

U.S. PATENT DOCUMENTS

2014/0166028 A1* 6/2014 Fuisz ................... A24D 1/002
131/328
2014/0348926 A1* 11/2014 Hoffman ................ A61K 31/17
424/489

FOREIGN PATENT DOCUMENTS

WO WO-2012035283 A1 * 3/2012 ........... A61K 9/2866

OTHER PUBLICATIONS

Gorgani et. al., Comprehensive Rev. in Food Sci. & Food Safety, publ. 2016, vol. 16, pp. 124-140 (Year: 2016).*
Cellai et al., "Rifaximin (L/105), A New Topical Intestinal Antibiotic: Pharmacokinetic Study After Single Oral Administration of 3H-Rifaximin to Rats", Chemioterapia, (1984), vol. III, pp. 373-377.
Descombe et al., "Pharmacokinetic Study of Rifaximin After Oral Administration in Healthy Volunteers", International Journal of Clinical Pharmacology Research, (1994), vol. XIV(2), pp. 51-56.
Gerard et al., "Rifaximin: a nonabsorbable rifamycin antibiotic for use in nonsystemic gastrointestinal infections", Expert Review of Anti-infective Therapy, (2005), vol. 3(2), pp. 201-211.
Ghanshyam et al., "A Comprehensive Review on Pharmacotherapeutics of Herbal Bioenhancers", The Scientific World Journal, (2012), vol. 2012, article ID 637953, pp. 1-34.
Marchi et al., "4-Deoxypyrido[1',2':1,2]imidazo[ 5,4-c ]rifamycin SV Derivatives. A New Series of Semisynthetic Rifamycins with High Antibacterial Activity and Low Gastroenteric Absorption", Journal of Medicinal Chemistry, (1985), vol. 28, pp. 960-963.
Venturini, "Pharmacokinetics of L/105, a New Rifamycin, in Rats and Dogs, after Oral Administration", (1983), Chemotherapy, vol. 29, pp. 1-3.
Venturini et al., "In Vitro and In Vivo Evaluation of L/105, a New Topical Intestinal Rifamycin" Chemioterapia, (1986), vol. V, pp. 257-262.

* cited by examiner

*Primary Examiner* — Sarah Pihonak
(74) *Attorney, Agent, or Firm* — MacMillan, Sobanski & Todd, LLC

(57) ABSTRACT

A pharmaceutical composition is provided for the treatment of systemic infections as well as colonic diseases. The composition comprises a therapeutically effective amount of rifaximin and a therapeutically effective amount of at least one alkaloid or derivative thereof. Methods and kits are also provided.

10 Claims, 2 Drawing Sheets

PHARMACEUTICAL COMPOSITIONS COMPRISING RIFAXIMIN

CROSS REFERENCE TO RELATED APPLICATIONS

This application claims priority to co-pending Indian Provisional Patent Application Serial Number 201621035173 filed on Oct. 14, 2016. This application is incorporated herein by reference, in its entirety.

FIELD

The present invention relates to a pharmaceutical composition comprising an antibacterial drug such as rifaximin and at least one alkaloid. The invention also relates to a process for preparing such pharmaceutical composition and its use for the treatment of systemic infections as well as colonic diseases.

BACKGROUND

One of the major obstacles to the development of highly potent pharmaceutical formulations is the poor water solubility of many drugs. Approximately 40% of potential drugs that are identified by pharmaceutical companies are poorly soluble in water, which greatly hinders their clinical use. Low water solubility limits the bioavailability and absorption of these agents.

Rifaximin is a semisynthetic antibiotic belonging to the rifamycin class of antimicrobial drugs exhibiting in vitro activity against Gram-positive, Gram-negative and anaerobic bacteria. Rifaximin acts by inhibiting bacterial ribonucleic acid (RNA) synthesis. Rifaximin is chemically named as [(2S,16Z,18E,20S,21S,22R,23R,24R,25S,26S, 27S,28E)-5,6,21,23,25-pentahydroxy-27-methoxy-2,4,11, 16,20,22,24,26-octamethyl-2,7 (epoxypentadeca-[1,11,13] trienimino)benzofuro[4,5-e]pyrido[1,2-a]-benzimidazole 1,15(2H)-dione,25-acetate]. Rifaximin has the following chemical formula.

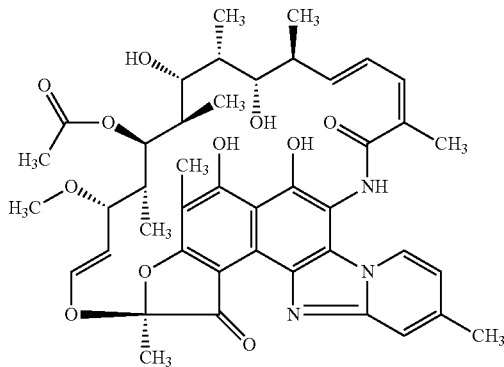

Rifaximin is commercially available under the trade name XIFAXAN®, as a 200 mg and 550 mg film coated oral tablets in USA and as XIFAXANTA® 200 mg, TARGAXAN® 550 mg in UK.

In USA, Rifaximin has been indicated for the treatment of traveler's diarrhea not caused by *Escherichia coli*, a microorganism which is not able to penetrate into GI mucosa and therefore remains in contact with gastrointestinal fluids, hepatic encephalopathy and Irritable Bowel Syndrome with Diarrhea.

In UK, Rifaximin 200 mg has been indicated for the treatment of travelers' diarrhea and 550 mg has been indicated for the reduction in recurrence of episodes of overt hepatic encephalopathy in patients ≥18 years of age.

Rifaximin is also approved for the treatment of pathologies whose etiology is in part or totally due to intestinal acute and chronic infections sustained by Gram-positive and Gram-negative bacteria, with diarrhea syndromes, altered intestinal microbial flora, summer diarrhea-like episodes, traveler's diarrhea and enterocolitis, pre- and post-surgery prophylaxis of the infective complications in gastro intestinal surgery; and hyperammonemia therapy as coadjutant.

Rifaximin is a poorly water-soluble and minimally absorbed (<0.4%) drug with in vitro activity against enteric Gram-negative bacteria including enteric pathogens. [Gerard L et al., Rifaximin, a non-absorbable rifamycin antibiotic for use in nonsystemic gastrointestinal infections. Expert Review of Anti-infective therapy, 3(2), 201-211, (2005)].

It has also been reported that rifaximin is characterized by negligible systemic absorption, due to its chemical and physical characteristics [Descombe J J et al., Pharmacokinetic study of rifaximin after oral administration in healthy volunteers. International Journal of Clinical Pharmacology Research, 14 (2), 51-56, (1994)].

Rifaximin has been described to be endowed with an antibacterial activity similar to the activity of rifampin [Venturini A. P. and Marchi E., Chemiotherapia, 5 (4), 257-256, (1986)]. However, its mechanism of action differs from rifampin in that it is not absorbed through the systemic route after oral administration [Venturini A. P., Chemotherapy, 29, 1-3, (1983) and Cellai L. et al., Chemiotherapia, 3, (6), 373-377, (1984)] due to the zwitterionic nature of the compound, which cannot be absorbed by the gastrointestinal tract [Marchi E. et al., Journal of Medicinal Chemistry, 28, 960-963, (1985)].

Hence in addition to poor water solubility, rifaximin has no systemic absorption, which poses a challenge to alleviate systemic infections as well as to formulate suitable compositions of rifaximin.

Although several strategies and formulations such as complexing rifaximin with cyclodextrins, rifaximin nanoparticles have been employed in the prior art to overcome the limitations of solubility and poor systemic absorption, there still remains a need to improve the systemic absorption of rifaximin and enable it for the treatment of systemic infections, particularly *Clostridium difficile* infection, infections caused by Gram-positive and Gram-negative bacteria as well as for the treatment of colonic diseases.

SUMMARY

In some embodiments, an object of the present invention is to provide a pharmaceutical composition comprising rifaximin and at least one alkaloid having improved solubility and systemic absorption.

In some embodiments, another object of the present invention is to provide a composition comprising rifaximin and at least one alkaloid for once or twice a day administration.

In some embodiments, yet another object of the present invention is to provide a composition comprising rifaximin and at least one alkaloid for once or twice a day administration with reduced dose.

In some embodiments, another object of the present invention is to provide a composition comprising rifaximin and at least one alkaloid in the form of a kit.

In some embodiments, another object of the present invention is to provide a method for treatment of systemic infections as well as colonic diseases which method comprises administering a pharmaceutical composition comprising rifaximin and at least one alkaloid.

In some embodiments, yet another object of the present invention is to provide the use of a pharmaceutical composition comprising rifaximin and at least one alkaloid for the treatment of systemic infections as well as colonic diseases.

According to an aspect of the present invention, there is provided a pharmaceutical composition comprising rifaximin and at least one alkaloid and one or more pharmaceutically acceptable excipients.

According to another aspect of the invention, there is provided a process for preparing a pharmaceutical composition comprising rifaximin and at least one alkaloid with at least one or more pharmaceutically acceptable excipients According to another aspect of the present invention there is provided a method for the treatment of systemic infections as well as colonic diseases which method comprises administering a pharmaceutical composition comprising rifaximin and at least one alkaloid according to the present invention to a patient in need thereof.

According to another aspect of the present invention there is provided the use of a pharmaceutical composition comprising rifaximin and at least one alkaloid according to the present invention in the manufacture of a medicament for the treatment of systemic infections as well as colonic diseases.

In some embodiments, pharmaceutical composition is provided comprising a therapeutically effective amount of rifaximin and a therapeutically effective amount of at least one alkaloid or derivative thereof.

In some embodiments, pharmaceutical composition is provided comprising a therapeutically effective amount of rifaximin and a therapeutically effective amount of at least one alkaloid or derivative thereof; and one or more pharmaceutically acceptable excipients comprising carriers, diluents, fillers, binders, lubricants, glidants, disintegrants, bulking agents, flavorants or any combination thereof.

In some embodiments, a method for treating systemic infections as well as colonic diseases is provided, the method comprising: administering a pharmaceutical composition comprising (i) a therapeutically effective amount of rifaximin; (ii) a therapeutically effective amount of at least one alkaloid or derivative thereof and (iii) one or more pharmaceutically acceptable excipients comprising carriers, diluents, fillers, binders, lubricants, glidants, disintegrants, bulking agents, flavourants or any combination thereof.

In some embodiments, a method of making a pharmaceutical composition that enhances the bioavailability of rifaximin is provided, the method comprising: mixing a therapeutically effective amount of rifaximin and a therapeutically effective amount of at least one alkaloid or derivative thereof with one or more pharmaceutically acceptable excipients to make the pharmaceutical composition.

In some embodiments, a kit for treating systemic infections as well as colonic diseases is provided, the kit comprising a therapeutically effective amount of rifaximin and a therapeutically effective amount of at least one alkaloid or derivative thereof, wherein the rifaximin is in a separate composition from the at least one alkaloid or derivative thereof.

In some embodiments, a method of enhancing the bioavailability of rifaximin is provided, the method comprising: providing a therapeutically effective amount of rifaximin and providing a therapeutically effective amount of at least one alkaloid or derivative thereof.

DETAILED DESCRIPTION

Figure 1:
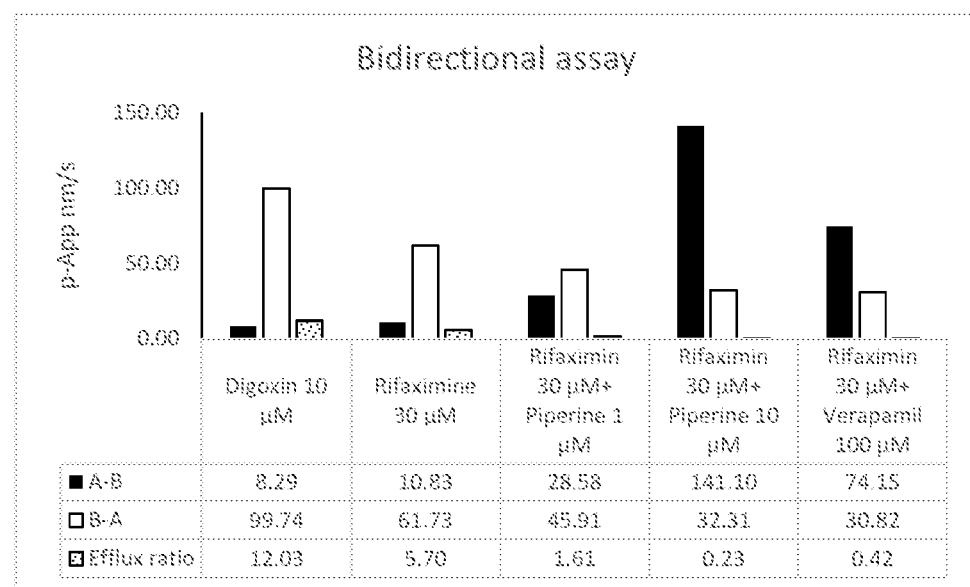
FIG. 1 depicts a bar graph of results from a bidirectional assay of Digoxine 10 μM, Rifaximin 30 μM, Rifaximin 30 μM+Piperine 1 μM, Rifaximin 30 μM+Piperine 10 μM and Rifaximin 30 μM+Verapamil 100 μM. Results showed that Rifaximin absorption is increased with piperine by decreasing the efflux ratio of Rifaximin

*Clostridium difficile* associated diarrhea (CDAD) has been reported with use of nearly all antibacterial agents, including rifaximin and such CDAD may range in severity from mild diarrhea to fatal colitis.

Treatment with antibacterial agents alters the normal flora of the colon which may lead to overgrowth of *C. difficile. C. difficile* produces toxins A and B which contribute to the development of CDAD. Hypertoxin producing strains of *C. difficile* cause increased morbidity and mortality, as these infections can be refractory to antimicrobial therapy and may require colectomy.

CDAD must be considered in all patients who present with diarrhea following antibiotic use. Careful medical history is necessary since CDAD has been reported to occur over two months after the administration of antibacterial agents. If CDAD is suspected or confirmed, ongoing antibiotic use not directed against *C. difficile* may need to be discontinued. Appropriate fluid and electrolyte management, protein supplementation, antibiotic treatment of *C. difficile*, and surgical evaluation should be instituted as clinically indicated.

Accordingly, administration of rifaximin for its currently approved indications such as traveler's diarrhea, hepatic encephalopathy and Irritable Bowel Syndrome with diarrhea may cause unwanted systemic infections such as *Clostridium difficile* associated diarrhea leading to discontinuation of therapy.

However, the inventors of the present invention have found that the systemic absorption of rifaximin can be facilitated or improved by providing rifaximin in combination with at least one alkaloid, preferably piperine, thus exhibiting enhanced therapeutic effect for systemic infections such as, but not limited to, *Clostridium difficile* infection and infections caused by Gram-positive and Gram-negative bacteria.

Further, rifaximin in combination with at least one alkaloid, preferably piperine can also be used for the treatment of colonic diseases such as, but not limited to, Irritable Bowel Syndrome with diarrhea.

Rifaximin: A nonabsorbable, broad spectrum antibiotic for reduction in the risk for recurrence of overt hepatic encephalopathy, Benjamin Barner et al, Jul. 1, 2010, Clinical Pharmacology.

Antibacterial and Antidiarrheal Activities of Plant Products against Enterotoxinogenic *Escherichia coli*, Toxins 2013 November; 5(11): 2009-2041. This article discloses that several plant products can be used for the management of Enterotoxigenic *Escherichia coli* induced travelers' diarrhea. Piperine (1-piperoylpiperidine) has shown to inhibit the gastric emptying of solids/liquids in rat and gastrointestinal transit of mice in a dose-dependent manner. It acts as a gastrointestinal motility inhibitor and has also a probable effect on prostaglandins.

WO2007047253 discloses methods of increasing the aqueous solubility of an antifungal azole using hydroxybutenyl cyclodextrins.

WO2010/067072 discloses complexes of rifaximin and process for preparing such complexes.

EP0858804 discloses use of oral rifaximin compositions in the treatment of diarrhea from cryptosporidiosis. The rifaximin formulations disclosed are in the dosage form of tablet, capsule, sugar coated tablet, granules or syrup for oral administration.

U.S. Pat. No. 5,352,679 discloses use of rifaximin in formulations for treatment of gastric dyspepsia caused by *Helicobacter pylori* bacteria. The rifaximin formulations disclosed are in the dosage form of tablet, capsule, sugar coated tablet, granules or syrup for oral administration.

WO2012035283 discloses compositions comprising rifaximin in the form of particles, wherein substantially all the particles have a particle size less than or equal to 2 micrometres.

Rifaximin in the Treatment of Recurrent *Clostridium difficile* Infection, E. Mattila et al, Alimentary Pharmacology & Therapeutics, 2013; 37(1):122-128.

*Clostridium difficile* Infection: New Insights Into Management, Sahil Khanna et al, Mayo Clin Proc. 2012 November; 87(11): 1106-1117.

Rifaximin Is Effective for the Treatment of *Clostridium difficile*—Associated Diarrhea: Results of an Open-Label Pilot Study, David T. Rubin et al, Gastroenterology Research and Practice, Volume 2011 (2011), Article ID 106978, 5 pages.

The term "rifaximin" is used in broad sense to include not only "rifaximin" per se but also its pharmaceutically acceptable derivatives thereof. Suitable derivatives include pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

The term "infection" includes any systemic infection or disease that occurs in the bloodstream such as *Clostridium difficile* infection and infections caused by Gram-positive and Gram-negative bacteria.

The term "therapeutically effective amount" or "effective amount" is such that when administered, the pharmaceutical composition results in the inhibition of the systemic infection. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired.

The term "treatment" or "treating" of a disease, virus or condition refers to executing a protocol that may include administering one or more drugs to a patient, in an effort to alleviate signs or symptoms of the disease, virus or condition. Alleviation can occur prior to signs or symptoms of the disease, virus or condition appearing, as well as after their appearance. Thus, treating or treatment includes reducing, preventing or prevention of the disease, virus or condition. In addition, treating or treatment does not require complete alleviation of signs or symptoms, does not require a cure, and specifically includes protocols that have only a marginal effect on the patient.

The fruit of black pepper (*Piper nigrum* L.) and long pepper (*Piper longum* L.) are both important medicinal herbs in Ayurvedic and Unani (traditional Indian) systems of medicine, wherein the remedy generally consists of mixtures of herbs. A wide range of the medicinal uses of black pepper are known and have been documented including its use in the treatment of leucoderma.

Piperine, the major alkaloid found in the fruit of black pepper (*Piper nigrum* L.; Piperaceae), stimulates the replication of melanocytes and induces the formation of melanocytic dendrites. Piperine is expected to cause the repopulation of vitiligo patches through a stimulatory effect on perilesional and follicular melanocytes.

Piperine is chemically known as (1-2E, 4E-piperinoylpiperidine) and is structurally represented as below.

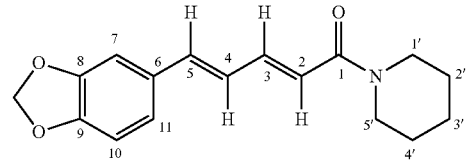

Piperine [E,E-(trans-trans)-piperine]\

In some embodiments, the alkaloid comprises piperine, tetrahydropiperine, cis-piperine, trans-piperine, cis-trans piperine, trans,cis piperine, cis,cis-piperine, trans,trans-piperine or a combination thereof. More preferably, the alkaloid is piperine or tetrahydropiperine and its analogs or derivatives. In some embodiments, the alkaloid increases plasma concentrations of rifaximin by 10%, 20, 30, 40, 50, 60, 70, 80, 90, 100% or higher in comparison to when the alkaloid is not used.

Piperine may enhance the drug bioavailability by promoting rapid absorption of drugs and nutrients by increasing blood supply to the gastrointestinal tract, decreasing hydrochloric acid secretion to prevent the breakdown of some drugs, increasing the emulsifying content of the gut, increasing enzymes like γ-glutamyl transpeptidase which participate in active and passive transport of nutrients to the intestinal cells.

Piperine may increase the drug bioavailability by inhibiting enzymes which participate in the biotransformation of drugs and thus preventing their inactivation and elimination. It also inhibits p-glycoprotein, the 'pump' protein that removes substances from cells and can decrease the intestinal production of glucuronic acid, thereby permitting more substances to enter the body in active form. Specifically, piperine inhibits CYP3A4, which is a major enzyme responsible for causing the metabolism of rifaximin ultimately causing an increase in the bioavailability of rifaximin.

Piperine has also been reported to occur in other *Piper* species i.e. *P. acutisleginum, album, argyrophylum, attenuatum, aurantiacum, betle, callosum, chaba, cubeba, guineense, hancei, khasiana, longum, macropodum, nepalense, novae hollandiae, peepuloides, retrokacturn, sylvaticum.*

Tetrahydropiperine is a structural analog of Piperine. The two double bonds at position 2 and 4 are saturated to give a tetrahydro analog. Tetrahydropiperine is chemically known as 5-(1,3-benzodioxol-5-yl)-1-piperidin-1-ylpentan-1-one and is structurally represented as shown below.

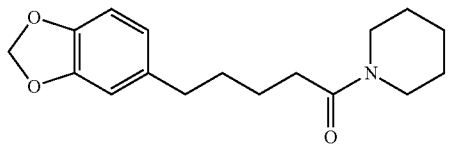 [SMILES: O=C(CCCCc1ccc2c(c1)OCO2)N1CCCCC1]

Tetrahydropiperine occurs like piperine naturally in black pepper (about 0.7% in black pepper oleoresin). Tetrahydropiperine can be synthesized from piperine which is previously extracted from black pepper oleoresin.

The term "analogs or derivatives" of tetrahydropiperine is used in broad sense to include alkyltetrahydropiperines, e.g. methyltetrahydropiperine or ethyltetrahydropiperine, dialkyltetrahydropiperines, e.g. dimethyltetrahydropiperine or diethyltetrahydropiperine, alkoxylated tetrahydropiperine, e.g. methoxy tetrahydropiperine, hydroxylated tetrahydropiperine, e.g. 1-[(5,3-benzodioxyl-5-yl)-1-hydroxy-2,4-pentadienyl]-piperine, 1-[(5,3-benzodioxyl-5-yl)-1-methoxy-2,4-pentadienyl]-piperine, halogenated tetrahydropiperine, e.g. 1-[(5,3-benzodioxyl-5-yl)-1-oxo-4-halo-2-pentenyl]-piperine and 1-[(5,3-benzodioxyl-5-yl)-1-oxo-2-halo-4-pentenyl]-piperine, dihydropiperine, alkyldihydropiperines, e.g. methyldihydropiperine or ethyldihydropiperine, dialkyldihydropiperines, e.g. dimethyldihydropiperine or diethyldihydropiperine, alkoxylated dihydropiperine, e.g. methoxy dihydropiperine, and halogenated dihydropiperine and their pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

In some embodiments, preferably the dose of piperine ranges from about 0.5 mg to about 400 mg and the dose of tetrahydropiperine ranges from about 0.5 mg to about 400 mg. In some embodiments, the dose of the piperine and/or the tetrahydropiperine ranges from about 0.5 mg, 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, to about 400 mg.

Preferably the dose of rifaximin ranges from about 5 mg to about 1000 mg and that of piperine ranges from about 5 mg to about 100 mg.

Preferably, the pharmaceutical compositions comprising rifaximin and piperine may be administered once or twice a day.

Preferably, the pharmaceutical compositions comprising rifaximin and piperine may be administered once or twice a day with reduced dose.

Preferably, the pharmaceutical composition may be provided in dosage forms such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid, liquid injectable or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention. In some embodiments, the pharmaceutical composition is administered via a syrup. A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

In some embodiments, a unit dosage from, such as a tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

The pharmaceutical compositions of the present invention comprise rifaximin and piperine. These active ingredients are formulated for simultaneous, separate or sequential administration. When the active ingredients are administered sequentially, either rifaximin or piperine, may be administered first. When administration is simultaneous, the active ingredients may be administered either in the same or different pharmaceutical compositions. Adjunctive therapy, i.e. where one active ingredient is used as the primary treatment and the other active ingredient(s) is/are used to assist that primary treatment is also an embodiment of the present invention.

Accordingly, there is provided a product comprising rifaximin and piperine as a combined preparation for simultaneous, separate or sequential use for treatment of systemic infections as well as colonic diseases.

In some embodiments, the pharmaceutical compositions of the present invention comprise rifaximin and tetrahydropiperine for simultaneous, separate or sequential use for treatment of systemic infections as well as colonic diseases.

The inventors of the present invention have also found that the bioavailability properties of the rifaximin may also be improved by nanosizing. In some embodiments, the pharmaceutical composition is administered via nanoparticles having a size of about 1 nanometer (nm) to about 50 nm. In some embodiments, the nanoparticles have a size of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nm.

In some embodiments, suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

In some embodiments, when the pharmaceutical composition is provided in unit dosage forms, as discussed above, the unit dosage form can be uncoated or coated.

These and other aspects of the present application will be further appreciated upon consideration of the following Examples, which are intended to illustrate certain particular embodiments of the application but are not intended to limit its scope, as defined by the claims.

EXAMPLES

Example 1—Rifaximin-Piperine Tablets

| Sr. No. | Ingredients | Quantity mg/tablet |
|---|---|---|
| 1. | Rifaximin | 50-1000 |
| 2. | Piperine | 10-100 |
| 3. | Glycerol palmitostearate | 10-150 |
| 4. | Microcrystalline cellulose (Avicel PH 101) | 5-100 |
| 5. | Silicon dioxide colloidal (Aerosil 200) | 40-170 |
| 6. | Edetate disodium | 1-7.5 |
| 7. | Sodium starch Glycolate | 30-60 |
| 8. | Magnesium stearate | 3-10 |
| 9. | Talc | 2-5 |
| | Coating | |
| 10. | Opadry ready mix | 10-45 |
| 11. | Purified water | qs |

Process:
1) Rifaximin, Piperine, microcrystalline cellulose, colloidal silicon dioxide, sodium starch glycolate, edetate disodium were sifted and added to a suitable blender.
2) Edetate disodium, Glycerol palmitostearate, Magnesium stearate and talc were sifted and added to the blend obtained in step (1), mixed, compressed into tablets and coated.

Example 2—Rifaximin-Piperine Capsules

| Sr. No. | Ingredients | Quantity mg/Capsule |
|---|---|---|
| 1. | Rifaximin | 5-250 |
| 2. | Piperine | 10-25 |
| 3. | Pregelatinized corn starch | 25-250 |
| 4. | Colloidal silicon dioxide | 1-15 |
| 5. | Magnesium stearate | 3-15 |
| 6. | Talc | 3-15 |
| 7. | Empty hard gelatin capsule shells | 1 unit |

Process:
1) Rifaximin and Piperine were sifted.
2) Pregelatinized corn starch, colloidal silicon dioxide and talc were sifted
3) The sieved powders obtained in step (1) & (2) were blended and mixed.
4) Magnesium stearate was sifted and added to the blend obtained in step (3).
5) The blend obtained in step (4) was then filled in the empty hard gelatin capsule shells.

Example 3—Rifaximin-Piperine Oral Suspension

| Sr. No. | Ingredients | Quantity mg/mL |
|---|---|---|
| 1. | Rifaximin | 5-500 |
| 2. | Piperine | 10-50 |
| 3. | Ascorbic acid | 5-15 |
| 4. | Sodium hydroxide | 1.5-5.0 |
| 5. | Edetate disodium (sodium EDTA) | 0.2-2.0 |
| 6. | Saccharin sodium | 0.1-1.0 |
| 7. | Sodium metabisulfite | 1-5 |
| 8. | Alcohol (ethanol, 95%) | 50-100 |
| 9. | Propylene glycol | 75-150 |
| 10. | Sorbitol (70% solution) | 75-150 |
| 11. | Glycerin (glycerol) | 200-350 |
| 12. | Sucrose | 250-400 |
| 13. | Quinoline yellow | 0.01-0.08 |
| 14. | Pineapple flavor | 0.1-0.5 |
| 15. | Purified water | q.s |

Process:
1) Purified water was heated to 90° C. to 95° C.
2) Required quantity of sucrose was added to the heated water of step (1) and mixed.
3) Propylene glycol, sorbitol, glycerin was added to the mixture of step (2) and mixed at high speed and cooled to a temperature of 50° C. with continuous mixing at slow speed.
4) Rifaximin was sifted and added to the solution obtained in step (3) with continuous mixing at high speed for to obtain a uniform suspension.
5) Ascorbic acid, edetate disodium and sodium metabisulfite were added to the suspension obtained in step (4) with continuous mixing.
6) Piperine was dissolved in ethanol and the solution was added to the suspension of step (4) while continuous stirring at slow speed.
7) Pineapple flavor was dissolved in part quantity of purified water and added to the suspension of step (4) with mixing at slow speed.
8) Sodium hydroxide and Saccharin sodium were dissolved in part quantity of purified water and added to the suspension of step (4) with slow mixing.
9) Quinoline yellow was dissolved in part quantity of purified water and the colour solution was transferred to the suspension of step (4) with slow mixing followed by mixing at high speed.
10) Volume was made up with purified water and suspension was again mixed at high speed.
11) pH of the suspension was checked and if required was adjusted with 10% citric acid or 10% sodium citrate solution.
12) The suspension was then filled in suitable bottles.

Example 4—Rifamixin-Piperine Powder for Oral Suspension

| Sr. No | Ingredients | Qty. mg/g |
|---|---|---|
| 1. | Rifamixin | 20-500 |
| 2. | Piperine | 5-50 |
| 3. | Polysorbate 80 | 0.25-0.50 |
| 4. | Simethicone | 0.6-1.0 |
| 5. | Xanthan gum | 10-20 |
| 6. | Silicon dioxide | 7.5-12.5 |
| 7. | Titanium dioxide | 15-20 |
| 8. | Sodium benzoate | 6-10 |

-continued

| Sr. No | Ingredients | Qty. mg/g |
|---|---|---|
| 9. | Cherry flavor, natural and artificial (microencapsulated) | 2.5-5.0 |
| 10. | Sucrose | q.s.t. 1000 mg |

Process:
1) Rifaximin, piperine, Xanthan gum, Silicon dioxide, Titanium dioxide, Sodium benzoate, Cherry flavor and sucrose were sifted.
2) Required quantity of Polysorbate 80 & semithicone were added on part of sifted sucrose and sifted.
3) The ingredients of step (1) & (2) were blended and the blend so obtained was filled in white translucent HDPE bottle with cap & sealed.

Example 5—Rifaximin-Piperine Tablets

| Sr. No. | Ingredients | Qty/Tab (mg) |
|---|---|---|
| 1. | Rifaximin | 20-750 |
| 2. | Piperine | 5-75 |

-continued

| Sr. No. | Ingredients | Qty/Tab (mg) |
|---|---|---|
| 3. | Microcrystalline cellulose | 10-35 |
| 4. | Lactose | 50-200 |
| 5. | Crosscarmellose Sodium | 2-10 |
| 6. | Povidone | 3-10 |
| 7. | Polysorbate 80 | 3-10 |
| 8. | Methylene chloride/water | q.s. |
| 9. | Hypromellose | 30-90 |
| 10. | Colloidal Anhydrous silica | 1-5 |
| 11. | Talc | 1-5 |
| 12. | Magnesium Stearate | 1-5 |
| | Coating | |
| 1. | Opadry ready mix | 10-20 |
| 2. | Purified water | qs |

Process
1) Rifaximin, Piperine, Microcrystalline cellulose, Lactose, Crosscarmellose Sodium were sifted and dry mixed.
2) Polysorbate 80 was dissolved in half quantity of methylene chloride/water mixture using overhead stirrer until a clear solution was obtained.
3) Binder solution was prepared by dissolving povidone in remaining quantity of methylene chloride/water under stirring until a clear solution was obtained.
4) Granulation of ingredients of step (1) was carried out using the binder solution of step (3) and Polysorbate 80 solution of step (2).
5) The granules were dried and sizing and then blended with Hypromellose, silicon dioxide, talc followed by lubrication with magnesium stearate.
6) The lubricated granules were then compressed into tablets and coated.

Preparative and Testing Methods

I) Material

Digoxin (known P-gp substrate), Rifaximin (CC74258), HBSS buffer, MES hydrate, HEPES powder, Fetal bovine serum (FBS), Minimum essential medium (MEM), Lucifer yellow, Piperine (P-gp inhibitor), Cobicistat (P-gp inhibitor).

Method

1) Caco-2 Cell Culture

Caco-2 cells were cultured in MEM media with 10% serum and seeded at a density of 75000 cells per mL and cultured for 21 days in a 24-well trans-well plate at 37° C., 5% $CO_2$. The monolayer integrity was checked intermittently (Day 0-21) using Trans Epithelial Electric Resistance (TEER). Cells were treated with drugs as follows:

2) Bidirectional Assay (A-B and B-A) to Study the Effect of Piperine (P-Gp Inhibitor) on the Permeability Plate Plan

TABLE 1

| | 1 | 2 | 3 | 4 | 5 | 6 |
|---|---|---|---|---|---|---|
| A<br>B | Digoxin<br>10 µM<br>(A – B) | Rifaximine<br>30 µM (A – B) | Rifaximin<br>100 µM (A – B) | Rifaximin<br>30 µM (A – B) + Piperine 1 µM | Rifaximin<br>30 µM (A – B) + Piperine 10 µM | Rifaximin<br>30 µM (A – B) + Verapamil 100 µM |
| C<br>D | Digoxin<br>10 µM<br>(B – A) | Rifaximin<br>30 µM (B – A) | Rifaximin<br>100 µM (B – A) | Rifaximin<br>30 µM (B – A) + Piperine 1 µM | Rifaximin<br>30 µM (B – A) + Piperine 10 µM | Rifaximin<br>30 µM (B – A) + Verapamil 100 µM |

Assay Protocol

For A-B, 400 µL samples were added to the wells as per the plate setup to the apical side in duplicates with 800 µL HBSS pH 7.4 in the basal wells. Samples were collected at 60, 90 and 120 minutes from the basal side. Mass balance samples at 0 and 120 minutes were collected from the apical side.

For B-A, 800 µL of the respective dilutions were added to the basal side in duplicates with 400 µL HBSS pH 7.4 in the apical wells. Samples were collected at 60, 90 and 120 minutes from the apical side. Mass balance samples at 0 and 120 minutes were collected from the basal side. The sample were analyzed on LCMS-MS.

At the end of the experiment the monolayer integrity was checked using and Lucifer yellow, calculating the % rejection of Lucifer yellow by incubating cells with 100 µg/mL Lucifer.

3) Data Analysis:

Papp was calculated as follows:
The apparent permeability (Papp) in units per second can be calculated by using the following equation,
For single point method:

$$Papp=(V/(T*A))*(C_0/C_t)$$

For multi-point method:

$$Papp=(dQ/dt)/(A*C_0)$$

$$\% \text{ Mass balance}=100-[C_{R120}*V_R+C_{D120}*V_D/C_0*V_D]$$

For Lucifer yellow,

% Lucifer Yellow Passage=[RFU(test)−RFU(blank)/
RFU(equilibrium)−RFU(blank)]*100

Permeability Classification:

TABLE 2

| Permeability | Papp (nm/s) |
| --- | --- |
| Low | <50 |
| Moderate | 50-200 |
| High | >200 |

Efflux ratio=$P$app $B$-$A$/$P$app $A$-$B$

Efflux ratio ≥2 indicates that the drug is a P-gp substrate

Results

Bidirectional Assay (FIG. 1)

TABLE 3

| Drug | Papp (nm/s) | | |
| --- | --- | --- | --- |
| | A-B | B-A | Efflux ratio |
| Digoxin 10 μM | 8.29 | 99.74 | 12.03 |
| Rifaximin 30 μM | 10.83 | 61.73 | 5.70 |
| Rifaximin 30 μM + Piperine 1 μM | 28.58 | 45.91 | 1.61 |
| Rifaximin 30 μM + Piperine 10 μM | 141.10 | 32.31 | 0.23 |
| Rifaximin 30 μM + Verapamil 100 μM | 74.15 | 30.82 | 0.42 |

Conclusions

Rifaximin is a known P-gp substrate. Rifaximin is a high permeable drug and piperine does not affect the permeability of Rifaximin across the caco-2 monolayer. Therefore, it can be concluded that the use of piperine decreases efflux ratio which in turn would increase its bioavailability.

Animal Study

The objective of the study was to check the effect of piperine on the bioavailability of Rifaximin after the administration of a single oral dose Study Design

TABLE 4

| Group | Treatment (Dose - mg/kg) | Dose Volume (mL/kg) | ROA | Formulation strength (mg/mL) |
| --- | --- | --- | --- | --- |
| G1 | Rifaximin (56) | 5 (vehicle) + 5 | PO | 11.2 (R) |
| G2 | Piperine (2) + Rifaximin (56) | 5 + 5 | PO | 0.4 (P) + 11.2 (R) |

Bioanalysis

Bioanalysis was performed using a fit-for-purpose LC-MS/MS method for the quantification of tenofovir in rat plasma samples. The calibration curve (CC) for the method consisted of nine non-zero calibration standards along with a double blank and zero standard samples. Study samples were analyzed along with three sets of quality control samples (18 QC samples; low, medium and high QC samples).

Pharmacokinetic Analysis

Figure 2:
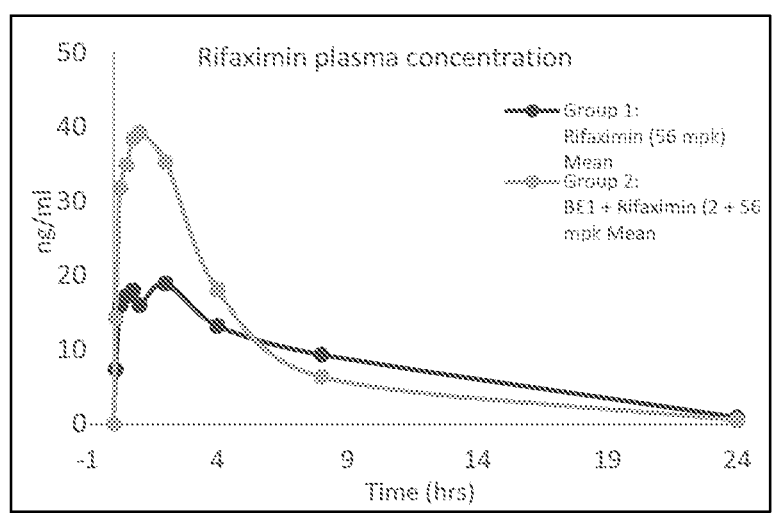
FIG. 2 depicts the peak plasma concentration (Cmax), time to achieve peak plasma concentration (Tmax), the area under the plasma concentration-time curve (AUC0-t and AUCinf), AUC Extra (%), elimination half-life (T1/2), clearance (CL), volume of distribution Vd (L/kg) and Mean residence time (MRT).

Plasma pharmacokinetic parameters were calculated using the non-compartmental analysis tool of Phoenix software (Version 6.3) and were determined from individual animals in each group. The peak plasma concentration (Cmax), time to achieve peak plasma concentration (Tmax), the area under the plasma concentration-time curve (AUC0-t and AUCinf), AUC Extra (%), elimination half-life (T1/2), clearance (CL), volume of distribution Vd (L/kg) and Mean residence time (MRT) were calculated from intravenous group. The peak plasma concentration (Cmax), time to achieve peak plasma concentration (Tmax), AUC0-t and AUCinf, AUC Extra (%), Mean residence time (MRT) and absolute oral bioavailability (F) were calculated from the oral group, as shown in FIG. 2.

Results

TABLE 5

| | Route Rifaximin at 56 mpk, PO Group | |
| --- | --- | --- |
| Formulation | Group 1 Rifaximin | Group 2 BE1 + Rifaximin |
| Dose (mg/kg) | 56 | 2 + 56 |
| Pk Parameters/Matrix | Plasma | Plasma |
| $C_{0(IV)}$ or $C_{max(PO)}$ (ng/mL) | 23.4 ± 2.18 (9.3) | 41.8 ± 10.3 (24.7) |
| $T_{max}$ (hr)[a] | 2.0 (0.25-8.0) | 1.0 (0.75-2.0) |
| AUClast (ng*hr/mL) | 170 ± 121 (71.2) | 200 ± 57 (28.4) |
| $T_{1/2}$ (hr) | 6.12 ± 2.16 (35.3) | 4.38 ± 2.04 (46.5) |
| $CL_{obs(IV)}$ or $CL/F_{(PO)}$ (mL/min/kg) | 6460 ± 2810 (43.6) | 4830 ± 1640 (34) |
| $Vz_{(IV)}$ or $Vz/F_{(PO)}$ (L/kg) | 3010 ± 540 (17.9) | 1840 ± 1160 (63.3) |
| Relative Bioavailability (F %) - [$AUC_{0-4\ hr}$] | — | 189 ± 51.6 (27.3) |

CONCLUSIONS

The C max of Rifaximin increases from 23.4 ng/ml to 41.8 ng/ml when administered with piperine. Also, the AUC increases from 170±121 to 200±57 when Rifaximin is dosed with piperine. The relative bioavailability of Rifaximin when administered along with piperine is 189%. Piperine significantly increases the bioavailability of Rifaximin The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

All patent and non-patent publications cited in this disclosure are incorporated herein in to the extent as if each of those patent and non-patent publications was incorporated herein by reference in its entirety. Further, even though the disclosure herein has been described with reference to particular examples and embodiments, it is to be understood that these examples and embodiments are merely illustrative of the principles and applications of the present disclosure. It is therefore to be understood that numerous modifications may be made to the illustrative embodiments and that other arrangements may be devised without departing from the spirit and scope of the present disclosure as defined by the following claims.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

We claim:

1. A pharmaceutical composition comprising a therapeutically effective amount of rifaximin and a therapeutically effective amount of at least one bioavailability enhancing agent comprising at least one piperine alkaloid selected from the group consisting of: piperine, tetrahydropiperine, cis-trans piperine, trans,cis-piperine, cis,cis-piperine, and a combination thereof:
   wherein the rifaximin is present in an amount of from about 5 mg to about 1000 mg, and
   wherein the piperine alkaloid is present in an amount from about 0.5 mg to about 400 mg.

2. The pharmaceutical composition of claim 1, further comprising one or more pharmaceutically acceptable excipients comprising carriers, diluents, fillers, binders, lubricants, glidants, disintegrants, bulking agents, flavorants or any combination thereof.

3. The pharmaceutical composition of claim 2, wherein the composition is in the form of a tablet, mini-tablet, granules, sprinkles, capsules, sachets, powders, pellets, disintegrating tablets, dispersible tablets, solution, suspension, emulsion, lyophilized powder or in the form of a kit.

4. The pharmaceutical composition of claim 2, wherein the pharmaceutical composition is formulated for use in the treating systemic infections and colonic diseases.

5. A kit for treating disease caused by caused by *Clostridium difficile* infection and infections caused by Gram-positive and Gram-negative bacteria, the kit comprising
   a therapeutically effective amount of rifaximin and
   a therapeutically effective amount of at least one bioavailability enhancing agent comprising at least one piperine alkaloid selected from the group consisting of: piperine, tetrahydropiperine, cis-trans piperine, trans,cis-piperine, cis,cis-piperine, and a combination thereof,
   wherein the rifaximin is in a separate composition from the at least one piperine alkaloid.

6. A method of treating systemic infections as well as colonic diseases in a patient in need of such treatment, the method comprising: administering a pharmaceutical composition comprising
   (i) a therapeutically effective amount of rifaximin;
   (ii) a therapeutically effective amount of at least one bioavailability enhancing agent comprising at least one piperine alkaloid selected from the group consisting of: piperine, tetrahydropiperine, cis-trans piperine, trans, cis-piperine, cis,cis-piperine, and a combination thereof; and
   (iii) one or more pharmaceutically acceptable excipients comprising carriers, diluents, fillers, binders, lubricants, glidants, disintegrants, bulking agents, flavorants or any combination thereof.

7. The method according to claim 6, wherein the diseases are caused by *Clostridium difficile* infection and infections caused by Gram-positive and Gram-negative bacteria.

8. A method of making a pharmaceutical composition that enhances the bioavailability of rifaximin, the method comprising:
   mixing a therapeutically effective amount of rifaximin and a therapeutically effective amount of at least one bioavailability enhancing agent comprising at least one piperine alkaloid selected from the group consisting of: piperine, tetrahydropiperine, cis-trans piperine, trans, cis-piperine, cis,cis-piperine, and a combination thereof with one or more pharmaceutically acceptable excipients to make the pharmaceutical composition.

9. A method of enhancing the bioavailability of rifaximin, the method comprising:
   providing a therapeutically effective amount of rifaximin and providing a therapeutically effective amount of at least one bioavailability enhancing agent comprising at least one piperine alkaloid selected from the group consisting of: piperine, tetrahydropiperine, cis-trans piperine, trans,cis-piperine, cis,cis-piperine, and a combination thereof.

10. The method of claim 9, wherein (i) the rifaximin is in a first composition and the at least one piperine alkaloid thereof is in a second composition; or (ii) rifaximin and the at least one piperine alkaloid thereof is combined in one composition.

* * * * *